United States Patent [19]

Stanley

[11] 4,376,736

[45] Mar. 15, 1983

[54] RATE AND YIELD ENHANCEMENT IN THE PREPARATION OF ETHOXYLATED QUATERNARY AMMONIUM BORATES USING ETHYLENE GLYCOL

[75] Inventor: Keith D. Stanley, Downers Grove, Ill.

[73] Assignee: Akzona Incorporated, Asheville, N.C.

[21] Appl. No.: 305,874

[22] Filed: Sep. 28, 1981

[51] Int. Cl.³ ............................................. C07F 5/04
[52] U.S. Cl. ............................................. 260/462 R
[58] Field of Search ................................... 260/462 R

[56] References Cited

U.S. PATENT DOCUMENTS

| | | | |
|---|---|---|---|
| 2,497,521 | 2/1950 | Trautman | 260/462 R |
| 3,373,170 | 3/1968 | Jones | 260/462 R X |
| 3,403,304 | 9/1968 | Ross et al. | 260/462 R X |
| 3,403,305 | 9/1968 | Santway et al. | 260/462 R X |
| 3,539,614 | 11/1970 | Ross et al. | 260/462 R |
| 3,639,234 | 1/1972 | Wixon | 260/462 R X |
| 4,265,664 | 5/1981 | Saischek et al. | 260/462 R X |

*Primary Examiner*—Helen M. S. Sneed
*Attorney, Agent, or Firm*—Francis W. Young; Daniel N. Christus

[57] ABSTRACT

This disclosure relates to a method for producing a class of quaternary ammonium borate compounds, and more particularly, to an improved method for producing quaternary ammonium borates by adding a glycol to the boric acid that provided the compound's anion so as to form a borate ester chelate complex having a rate-enhancing effect.

42 Claims, No Drawings

RATE AND YIELD ENHANCEMENT IN THE PREPARATION OF ETHOXYLATED QUATERNARY AMMONIUM BORATES USING ETHYLENE GLYCOL

BACKGROUND OF THE INVENTION

Quaternary ammonium borates are compounds useful in the textile fabric softener art, and are disclosed in U.S. patent application Ser. No. 190,550, filed by Richmond et al., on Sept. 28, 1980, and entitled, "Alkoxylated Quaternary Ammonium Borates." A typical method for manufacturing the compounds disclosed therein comprises treating an amine with boric acid, and then treating the resulting mixture with an alkylene oxide. This process is generally suitable for manufacturing the instant compounds, but is unsatisfactory in some respects. If the amine remains in its free state rather than being quaternized to the quarternary ammonium borate, the resulting compound is less efficacious as a fabric softener or in other applications. A stoichiometric excess of ethylene oxide is required to ensure an adequate conversion of the free amine to the quaternary product. However, the excessive use of ethylene oxide itself increases the production of undesirable side products, such as the carcinogenic dioxanes. Another disadvantage of the above method is the relatively slow reaction rate, which in itself increases dioxane levels and also increases production costs. Finally, the above method results in a compound having a Gardner color of 5 or more. A quaternary compound having a lower Gardner color is preferable in that it can be mixed with inactive ingredients to yield a commercial fabric softening formulation having a desirable light pink or blue color whereas a quaternary having a high Gardner color must first be bleached with a peroxide to lower the color to within the preferred range before mixing with the inerts.

Processes for manufacturing other quaternary ammonium compounds said to be useful as antistatics are described in U.S. Pat. No. 2,897,170, issued to Gruber on July 28, 1979, and entitled "Antistatic Treatment with a Quaternary Ammonium Compound containing a Polyetheneoxy Grouping and Products Thereof," and in U.S. Pat. No. 4,139,477, issued to Hayek et al. on Feb. 13, 1979, and entitled "Fabric Conditioning Compositions." Gruber discloses a quaternary ammonium compound that is typically prepared by mixing a tertiary amine with ethylene oxide and an anion containing acid in the presence of a solvent such as water. More specifically, the heated tertiary amine is dissolved in a secondary or tertiary alcohol and to the resulting solution is added from 40 to 80% of the theoretical quantity of acid required for complete neutralization of the amine. The resulting solution is heated to reflux and ethylene oxide is added at such a rate that moderate reflux takes place. This reaction may require as long as eleven hours to complete, and the method does not disclose the use of a diol as a reaction rate enhancer. In addition, Gruber does not disclose ethoxylated quaternary ammonium borates.

Hayek discloses an ethoxylated quaternary ammonium compound that is typically prepared by combining hydrogenated tallowamine with ethylene oxide and then heating the reaction mixture for about 10 hours. The polyoxyethylene chains are extended by adding a 50% dispersion of sodium hydride in mineral oil and additional ethylene oxide. After addition of glacial acetic acid to neutralize the sodium hydroxide formed in the reaction, dimethyl sulfate is added to produce a quaternary ammonium methyl sulfate salt. Finally, a mixture of saturated alcohols and the codistilling hydrocarbons, as derived from alcohol manufactured by ethylene polymerization, is added to the quaternary ammonium methyl sulfate salt. The composition thus prepared has a Gardner color of 5; no diol is used in its preparation.

SUMMARY OF THE INVENTION

The present invention is an improved method of producing an ethoxylated quaternary ammonium borate from an amine or diamine, ethylene oxide, and boric acid which comprises adding a diol to the anion-providing boric acid so as to form a reaction rate-enhancing borate ester chelate complex. Another aspect of the invention comprises adding the amine or diamine to the borate ester in the presence of a solvent to form a reaction mixture to which the ethylene oxide is added, the solvent being selected from the group consisting of isopropyl alcohol, water, ethanol, methanol, acetone, dimethoxyethane, ethyl acetate, and chloroform. A still further aspect of the invention comprises using ethylene glycol as the preferred diol.

The present invention is a method that is advantageous in many respects over those disclosed in the prior art. Diols increase the reaction rate and thereby lower both production costs and the amount of deleterions substances, such as dioxanes, in the quaternary ammonium compounds. The diols further reduce the Gardner color of the quaternary compounds sufficiently so that it is unnecessary to bleach them with peroxides. Further, the novel method reduces the amount of ethylene oxide necessary for adequate conversion of the amine or diamine to the quaternary ammonium compound. Lower amounts of free amine are present in the quaternary ammonium compound upon completion of the reaction, as a result of the higher conversion to the latter. The quaternary compound thus contains more active ingredient for a given volume of the product. Other advantages of the invention will appear in the rest of this specification and in the claims hereinbelow.

DESCRIPTION OF THE PREFERRED EMBODIMENTS

Amines, diamines, or ether amines may be used as the starting materials for the ethoxylated quaternary ammonium borates that may be prepared by the method of the invention. Amines include those compounds having the general formula,

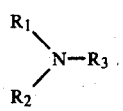

wherein $R_1$, $R_2$, and $R_3$ are either aryl, or straight or branched-chain alkyl radicals, or —H. For fabric softening compositions, straight chain alkyl radicals are preferred. Most preferred amines are the primary amines, that is, those having the general formula,

wherein R is a straight chain alkyl radical. These primary amines typically include long-chain alkyl groups derived from fatty acids, as for example the ARMEEN ® aliphatic amines produced by the Armak Company, Industrial Chemicals Division, 300 S. Wacker Dr., Chicago, Ill. 60606.

Diamines include those compounds having the general formula,

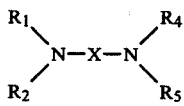

wherein $R_1$, $R_2$, $R_4$ and $R_5$ are either aryl, or straight or branched-chain alkyl radicals, or —H, and wherein X is either an alkylene or aryl group. For fabric softening compositions, straight chain alkyl radicals are preferred for the R groups and alkylene groups are preferred for X. Most peferred are diamines of the general formula,

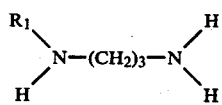

wherein $R_1$ is a long chain alkyl group derived from tallow, coco, soya, or oleic acids, as for example the DUOMEEN ® aliphatic diamines produced by the Armak Company, Industrial Chemicals Division.

Ether amines include those compounds having the general formula,

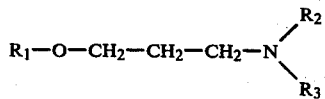

wherein $R_1$, $R_2$, and $R_3$ are either straight or branched-chain alkyl radicals, and wherein $R_2$ and $R_3$ may also be —H. For fabric softening compositions, straight chain alkyl radicals are preferred for the $R_1$ group, and the most preferred ether amines are of the general formula,

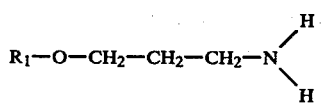

as for example the ARMEEN ® ether amines produced by the Armak Company, Industrial Chemicals Division.

To the amine, diamine, or ether amine is added a borate ester chelate complex produced by combining boric acid and a diol, that is, an organic compound having two OH groups, as for example, hexylene glycol, also known as 2-methyl-2,4-pentandiol [CH₃CCH₃)(OH)CH₂CH(OH)CH₃], propylene glycol (CH₃—CHOH-CH₂—OH), or the preferred diol, ethylene glycol (CH₂OH—CH₂OH). The mole ratio of the diol to the boric acid may be between 0.5:1 and 10:1, and is most preferably 1:1.

A reaction mixture includes the amine, diamine or ether amine and the borate ester in the presence of a solvent, the solvent being selected from the group consisting of water, ethanol, methanol, acetone, dimethoxyethane, ethyl acetate, chloroform, or the preferred solvent, isopropyl alcohol. The weight ratio of the solvent to the amine may be between 0.01:1 and 1:1, and is preferably between 0.01:1 and 0.15:1.

Finally, an excess of ethylene oxide is added under pressure to the reaction mixture.

The preferred reaction temperature is between 25° C. and 150° C., and the most preferred temperature is in the range of 70° C. to 120° C. The preferred reaction pressure is between 20 and 50 pounds per square inch gauge.

The borate ester chelate complex is disclosed on page 298 of *Advanced Inorganic Chemistry, A Comprehensive Text* by F. Albert Cotton and Geoffrey Wilson, Fourth edition, John Wiley and Sons, New York, N.Y., 1980, ISBN-0-471-02775-8, QD 151.2, .C68. The borate ester chelate complex formed is of the formula,

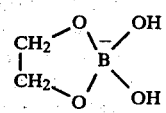

and in 1:1 diol-boric acid complexes, the acidity of the OH groups is known to exceed that in boric acid ($H_3BO_3$ or $B(OH)_3$).

The novel method is best disclosed by the following preferred embodiments, which are intended to be merely exemplary and not limiting.

EXAMPLE 1

A two liter Parr 316 stainless steel autoclave having a nitrogen purge line attached thereto is charged with 398.1 grams (1.170 gram moles) of DUOMEEN ® T, a diamine that is manufactured by the Armak Company, Chicago, Ill. and more commonly known as N-tallow-1,3-diaminopropane. The autoclave includes internal cooling coils and an electrically-heated jacket, and further includes an ethylene oxide reservoir in communication therewith. To the DUOMEEN ® T is added 180.8 grams (2.925 gram moles) of boric acid, 145.3 grams (2.340 gram moles) of ethylene glycol, and 135.7 grams of isopropyl alcohol, a solvent. The mixture is heated to about 80° C. with stirring so as to ensure the dissolution of the boric acid. When the mixture reaches 80° C., the autoclave is purged three times with 45 psig nitrogen to reduce the potential for peroxide formation. After the third purging, 10 psig remains in the autoclave. Ethylene oxide is then added to the reaction mixture at about 20 psig, with the mixture at about 90° C. After approximately 80 minutes, 1.47 gram moles have been added. The rate of ethylene oxide addition is increased, and during the next several hours an additional 4.39 gram moles are added and digested. After a reaction time of 4 hours, 15 minutes, there is 75% conversion of the diamine to the quaternary compound, where present conversion is defined as [milliequivalents of quaternary compound in end reaction mixture ÷ (milliequivalents of quaternary compound in end reaction mixture + milliequivalents of free amine in end reaction mixture)]×100. The stoichiometrically required mole ratio of ethylene oxide to diamine for complete reaction is 5.0, and in the present reaction the actual mole ratio is 5.01. This contrasts with a control reaction in which DUOMEEN ® T was reacted with boric acid, isopropyl alcohol, and ethylene oxide, but without ethylene glycol. In that reaction, the ratio of ethylene oxide to diamine was 6.16 and the percent conversion was 46.4%.

EXAMPLE 2

A one-liter Parr 316 stainless steel autoclave having a nitrogen purge line attached thereto is charged with 208.5 grams (0.564 gram moles) of ARMEEN ® 2C, a secondary amine manufactured by the Armak Company, Chicago, Ill., and more commonly known by its chemical name, dicocoamine. The autoclave includes internal cooling coils and an electrically-heated jacket and further includes a ethylene oxide reservoir in communication therewith. To the ARMEEN ® 2C is added 43.6 grams (0.704 gram moles) of boric acid, 43.7 grams (0.704 gram moles) of ethylene glycol, and 39.0 grams of mineral oil, a solvent. The mixture is heated to about 90° C. with stirring or agitation so as to ensure the dissolution of the boric acid. When the mixture reaches 90° C., the autoclave is twice purged with 45 psig nitrogen to reduce the potential for peroxide formation, 8 psig pressure remaining in the autoclave after the second purging. Ethylene oxide is then added to the reaction mixture, with the reactor at about 40 psig and the ethylene oxide reservoir at about 50 psig. After approximately 60 minutes, 1.72 gram moles have been added. During the next several hours an additional 2.56 gram moles of ethylene oxide are added and digested. After a reaction time of 4 hours and 30 minutes, there is 97.5% conversion of the secondary amine to the quaternary compound, and the product has a Gardner color of 6. The stoichiometrically required mole ratio of ethylene oxide to secondary amine for complete reaction is 2, and in the present reaction the actual mole ratio is 4.54. This contrasts with three control reactions in which ARMEEN ® 2C was reacted with boric acid, ethylene oxide, and in two reactions, mineral oil, but without ethylene glycol. Those reactions required reaction times of 5 hours 51 minutes, 5 hours 30 minutes, and 5 hours, 10 minutes; the ratios of ethylene oxide to secondary amine were 5.06, 4.67, and 4.46; and the percent conversions were 81.2, 86.6, and 86.2, respectively. The Gardner color of the compound formed in the second of the control reactions was 8.

EXAMPLE 3

The one-liter Parr 316 stainless steel autoclave with nitrogen line, ethylene oxide reservoir and jacket described in Example 2 is charged with 219.5 grams (0.918 gram moles) of ARMEEN ® DMCD, a dimethyl alkyl tertiary amine manufactured by the Armak Company, Chicago, Ill., and more commonly known by its chemical name, N,N-dimethylcocoamine, 71.0 grams (1.15 gram moles) of boric acid, and 71.3 grams (1.15 gram moles) of ethylene glycol. The mixture is heated to about 90° C. with agitation. When the mixture attains 90° C., the autoclave is twice purged with 50 psig nitrogen to reduce the potential for peroxide formation, 8 psig pressure remaining in the autoclave after the second purging. 0.94 gram moles of ethylene oxide is added to the mixture with the reservoir at 50 psig and the autoclave at 45 psig. During the next several hours, an additional 0.90 gram mole of ethylene oxide is added and digested. After a reaction time of 2 hours, 55 minutes, there is 94.6% conversion of the tertiary amine to the quaternary compound. The stoichiometrically required mole ratio of ethylene oxide to tertiary amine for complete reaction is 1, and in the present reaction the actual mole ratio is 2.00. In a control reaction requiring 3 hours, 23 minutes, ARMEEN ® DMCD was reacted with boric acid and ethylene oxide, but without ethylene glycol. 2.55 moles of ethylene oxide per mole of tertiary amine were required and resulted in a 51.8 percent conversion.

EXAMPLE 4

The one-liter Parr 316 stainless steel autoclave with nitrogen line, ethylene oxide reservoir, and jacket described in Example 2 is charged with 285.6 grams (0.569 gram moles) of ARMEEN ® 2Ht, a secondary amine manufactured by the Armak Company, Chicago, Ill., and more commonly known by its chemical name, di(-hydrogenated-tallow)amine, 44.0 grams (0.711 gram mole) boric acid, 44.2 grams (0.711 gram moles) of ethylene glycol, and 53.9 grams of isopropyl alcohol, a solvent. The mixture is heated to about 75° C. with stirring, and the autoclave purged once with 50 psig nitrogen to reduce the potential for peroxide formation. During approximately the next hour, 2.21 gram moles of ethylene oxide is added to the autoclave, with the ethylene oxide reservoir at 40–45 psig. Digestion of the ethylene oxide continues over the next 3 hours. After a reaction time of 4 hours, 30 minutes, there is 90.2% conversion of the secondary amine to the quaternary compound and the product contains a trace (less than 2 ppm) of dioxane and has a Gardner color of 3–4. The stoichiometrically required mole ratio of ethylene oxide to secondary amine for complete reaction is 2, and in the present reaction the mole ratio is 3.88. This contrasts with a control reaction in which ARMEEN ® 2HT was reacted with boric acid, isopropyl alcohol, and ethylene oxide, but without ethylene glycol. That reaction required 10 hours, 50 minutes; the ratio of ethylene oxide to secondary amine was 4.16, and the percent conversion was 86.7. The product contained 66 ppm dioxane and had a Gardner color of 5–6.

EXAMPLE 5

The one-liter Parr 316 stainless steel autoclave with nitrogen line, ethylene oxide reservoir, and jacket described in Example 2 is charged with 267.8 grams (0.533 gram mole) of ARMEEN ® 2HT, 41.2 grams (0.667 gram mole) of boric acid, 20.7 grams (0.334 gram mole) of ethylene glycol, and 50.5 grams of isopropyl alcohol, a solvent. The mixture is heated to about 75° C. with stirring, and the autoclave purged once with 50 psig nitrogen, with 8 psig pressure remaining in the autoclave after the purging. During the next hour, 1.87 gram moles of ethylene oxide is added to the autoclave, with the ethylene oxide reservoir at approximately 45 psig. Digestion of the ethylene oxide continues for nearly the next five hours. After a total reaction time of 6 hours, 10 minutes, there is a 91.2% conversion of the secondary amine to the quaternary compound, and the product contains 15 parts per million (ppm) of dioxane and has a Gardner color of 4–5. The stoichiometrically required mole ratio of ethylene oxide to secondary amine for complete reaction is 2, and the mole ratio in the present reaction is 3.51. This contrasts with a control reaction in which ARMEEN ® 2HT was reacted with boric acid, isopropyl alcohol, and ethylene oxide, but without ethylene glycol. That reaction required 10 hours, but the ratio of ethylene oxide to secondary amine was 4.16, and the percent conversion was 86.7. The product contained 66 ppm dioxane and had a Gardner color of 5–6.

EXAMPLE 6

The one-liter Parr 316 stainless steel autoclave of Example 2 is charged with 193.3 grams (0.743 gram moles) of ARMEEN ® EA-13, an ether amine derived from a linear or branched-chain alcohol and having the molecular structure, $$R-O-CH_2-CH_2-CH_2NH_2$$

wherein R is the alkyl portion of linear or branched-chain tridecyl alcohol. ARMEEN ® EA-13 is a product of the Armak Company, Chicago, Ill. Also added to the reactor is 57.5 grams (0.929 gram moles) of boric acid, 57.3 grams (0.929 gram moles) of ethylene glycol, and 25.1 grams of isopropyl alcohol, a solvent. The mixture is heated to about 75° C. with stirring and the autoclave purged once with 50 psig nitrogen, with 8 psig pressure remaining in the autoclave after the purging. During the next 70 minutes, 3.04 gram moles of ethylene oxide is added to the autoclave, with the ethylene oxide reservoir at approximately 45 psig. Digestion of the ethylene oxide continues for the next two hours, and after the total reaction time of 3 hours, 10 minutes, there is a 87.8% conversion of ether amine to the quaternary compound. The stoichiometrically required mole ratio of ethylene oxide to this essentially primary ether amine is 3, and the mole ratio in the present reaction is 4.09. This contrasts with a control reaction in which ARMEEN ® EA-13 is reacted with boric acid, isopropyl alcohol, and ethylene oxide, but without ethylene glycol, which had a reaction time of 5 hours, 30 minutes, a 74.6% conversion, and an ethylene oxide: ether amine molar ratio of 4.85.

EXAMPLE 7

The one-liter Parr 316 stainless steel autoclave of Example 2 is charged with 257.8 grams (0.514 gram moles) of the secondary amine, ARMEEN ® 2HT, 39.7 grams (0.642 gram moles) of boric acid, 26.8 grams (0.352 gram moles) of propylene glycol, and 38.8 grams of isopropyl alcohol, a solvent. The mixture is heated to 75° C. with stirring, and the autoclave purged once with 45 psig nitrogen, with 8 psig pressure remaining in the autoclave after the purging. During the next 35 minutes, 1.80 gram moles of ethylene oxide is added to the autoclave through the ethylene oxide reservoir at 47 psig. Digestion of the ethylene oxide continues over the next 5 hours, and after a reaction time of 5 hours, 33 minutes, there is an 86.7% conversion of the secondary amine to the quaternary compound. The stoichiometrically required mole ratio of ethylene oxide to a secondary amine is 2, and the mole ratio in the present reaction is 3.50. This contrasts with a control reaction in which ARMEEN ® 2HT is reacted with boric acid, isopropyl alcohol, and ethylene oxide, but not with ethylene glycol. This control reaction had a reaction time of 10 hours, an 86.7% conversion, and an ethylene oxide: secondary amine mole ratio of 4.16.

EXAMPLE 8

The one-liter Parr 316 stainless steel autoclave of Example 2 is charged with 256.3 grams (0.511 gram moles) of the secondary amine, ARMEEN ® 2HT, 39.5 grams (0.638 gram moles) of boric acid, 37.7 grams (0.319 gram moles) of hexylene glycol, and 37.9 grams of isopropyl alcohol, a solvent. The mixture is heated to 75° C. with stirring, and the autoclave purged once with 45 psig nitrogen, with 8 psig pressure remaining in the autoclave after the purging. During the next 31 minutes, 1.79 gram moles of ethylene oxide is added to the autoclave through the ethylene oxide reservoir at 47 psig. Digestion of the ethylene oxide continues over the next 5 hours, and after a reaction time of 5 hours, 33 minutes, there is an 82.7% conversion of the secondary amine to the quaternary compound. The mole ratio of ethylene oxide to secondary amine in the present reaction is 3.50. This contrasts with a control reaction in which ARMEEN ® 2HT is reacted with boric acid, isopropyl alcohol, and ethylene oxide but not with ethylene glycol. This control reaction had a reaction time of 10 hours, an 86.7% conversion, and an ethylene oxide: secondary amine mole ratio of 4.16.

From the foregoing illustrative examples, it is evident that the addition of a glycol to the components used in the prior art to manufacture a quaternary borate compound speeds the production of that compound, and surprisingly results in lower use of ethylene oxide for its production, improved color, and lower dioxane content.

What I claim is:

1. A method of producing an ethoxylated quaternary ammonium borate from an amine, diamine or ether amine, ethylene oxide, and boric acid, the improvement comprising adding a diol to said boric acid to form a borate ester chelate complex.

2. The method as set forth in claim 1, wherein said diol is ethylene glycol.

3. The method as set forth in claim 1, further comprising adding said amine or said diamine or said ether amine to said borate ester in the presence of a solvent to form a reaction mixture, and then adding ethylene oxide to said reaction mixture.

4. The method as set forth in claim 2, further comprising adding said amine or said diamine or said ether amine to said borate ester in the presence of a solvent to form a reaction mixture, and then adding said ethylene oxide to said reaction mixture.

5. The method as set forth in claim 3, wherein said solvent is selected from the group consisting of: isopropyl alcohol, water, ethanol, methanol, acetone, dimethyoxyethane, ethyl acetate, and chloroform.

6. The method as set forth in claim 4, wherein said solvent is selected from the group consisting of: isopropyl alcohol, water, ethanol, methanol, acetone, dimethyoxyethane, ethyl acetate, and chloroform.

7. A method of producing an ethoxylated quaternary borate, said method comprising blending a diol and boric acid to form a borate ester chelate complex, adding said chelate complex in the presence of a solvent to an amine of the formula,

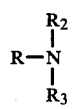

wherein $R_1$, $R_2$, and $R_3$ are either straight or branched-chain alkyl or aryl radicals or —H, and adding ethylene oxide to said amine and said chelate complex.

8. The method as set forth in claim 7, wherein the mole ratio of ethylene glycol to boric acid is between 0.5:1.0 and 10.0:1.0.

9. The method as set forth in claim 7, wherein said method is reacted at a temperature of between 25° C. and 150° C.

10. The method as set forth in claim 7, wherein said method is reacted at a temperature of between 70° C. and 120° C.

11. The method as set forth in claim 8, wherein said method is reacted at a temperature of between 70° C. and 120° C.

12. The method as set forth in claim 7, wherein the weight ratio of said solvent to said amine is between 0.01:1 and 1:1.

13. The method as set forth in claim 8, wherein the weight ratio of said solvent to said amine is between 0.01:1 and 1:1.

14. The method as set forth in claim 9, wherein the weight ratio of said solvent to said amine is between 0.01:1 and 1:1.

15. The method as set forth in claim 10, wherein the weight ratio of said solvent to said amine is between 0.01:1 and 1:1.

16. The method as set forth in claim 11, wherein the weight ratio of said solvent to said amine is between 0.01:1 and 1:1.

17. The method as set forth in claim 16, wherein said solvent is selected from the group consisting of isopropyl alcohol, water, ethanol, methanol, acetone, dimethoxyethane and ethyl acetate.

18. A method of producing an ethoxylated quaternary borate, said method comprising blending equimolar amounts of ethylene glycol and boric acid to form a borate ester chelate complex, adding said chelate complex in the presence of isopropyl alcohol to an amine of the formula,

wherein $R_1$ is a straight-chain alkyl radical and wherein the weight ratio of isopropyl alcohol to said amine is between 0.01:1 and 0.15:1, said method being reacted at a temperature of between 70° C. and 120° C., and at a gauge pressure of between 20 and 50 pounds per square inch, and adding ethylene oxide to said amine and said chelate complex.

19. A method of producing an ethoxylated quaternary borate, said method comprising blending a diol and boric acid to form a borate ester chelate complex, adding said chelate complex in the presence of a solvent to a diamine of the formula,

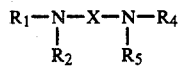

wherein $R_1$, $R_2$, $R_4$, and $R_5$ are either straight or branched-chain alkyl or aryl radicals or —H, and wherein X is either an alkylene or aryl group, and adding ethylene oxide to said amine and said chelate complex.

20. The method as set forth in claim 19, wherein the mole ratio of ethylene glycol to boric acid is between 0.5:1.0 and 10.0:1.0.

21. The method as set forth in claim 19, wherein said method is reacted at a temperature of between 25° C. and 150° C.

22. The method as set forth in claim 19, wherein said method is reacted at a temperature of between 70° C. and 120° C.

23. The method as set forth in claim 20, wherein said method is reacted at a temperature of between 70° C. and 120° C.

24. The method as set forth in claim 19, wherein the weight ratio of said solvent to said amine is between 0.01:1 and 1:1.

25. The method as set forth in claim 20, wherein the weight ratio of said solvent to said amine is between 0.01:1 and 1:1.

26. The method as set forth in claim 21, wherein the weight ratio of said solvent to said amine is between 0.01:1 and 1:1.

27. The method as set forth in claim 22, wherein the weight ratio of said solvent to said amine is between 0.01:1 and 1:1.

28. The method as set forth in claim 23, wherein the weight ratio of said solvent to said amine is between 0.01:1 and 1:1.

29. The method as set forth in claim 28, wherein said solvent is selected from the group consisting of isopropyl alcohol, water, ethanol, methanol, acetone, dimethoxyethane and ethyl acetate.

30. A method of producing an ethoxylated quaternary borate, said method comprising blending equimolar amounts of ethylene glycol and boric acid to form a borate ester chelate complex, adding said chelate complex in the presence of isopropyl alcohol to a diamine of the formula,

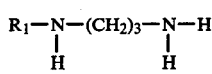

wherein $R_1$ is a straight-chain alkyl radical and wherein the weight ratio of isopropyl alcohol to said diamine is between 0.01:1 and 0.15:1, said method being reacted at a temperature of between 70° C. and 120° C., and at a gauge pressure of between 20 and 50 pounds per square inch, and adding ethylene oxide to said amine and said chelate complex.

31. A method of producing an ethoxylated quaternary borate, said method comprising blending a diol and boric acid to form a borate ester chelate complex, adding said chelate complex in the presence of a solvent to an amine of the formula,

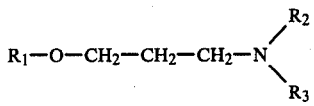

wherein $R_1$, $R_2$, and $R_3$ are either straight or branched-chain alkyl radicals and wherein $R_2$ and $R_3$ may also be —H, and adding ethylene oxide to said ether amine and said complex.

32. The method as set forth in claim 31, wherein the mole ratio of ethylene glycol to boric acid is between 0.5:1.0 and 10.0:1.0.

33. The method as set forth in claim 31, wherein said method is reacted at a temperature of between 25° C. and 150° C.

34. The method as set forth in claim 31, wherein said method is reacted at a temperature of between 70° C. and 120° C.

35. The method as set forth in claim 32, wherein said method is reacted at a temperature of between 70° C. and 120° C.

36. The method as set forth in claim 31, wherein the weight ratio of said solvent to said ether amine is between 0.01:1 and 1:1.

37. The method as set forth in claim 32, wherein the weight ratio of said solvent to said amine is between 0.01:1 and 1:1.

38. The method as set forth in claim 33, wherein the weight ratio of said solvent to said ether amine is between 0.01:1 and 1:1.

39. The method as set forth in claim 34, wherein the weight ratio of said solvent to said ether amine is between 0.01:1 and 1:1.

40. The method as set forth in claim 35, wherein the weight ratio of said solvent to said ether amine is between 0.01:1 and 1:1.

41. The method as set forth in claim 40, wherein said solvent is selected from the group consisting of isopropyl alcohol, water, ethanol, methanol, acetone, dimethoxyethane and ethyl acetate.

42. A method of producing an ethoxylated quaternary borate, said method comprising blending equimolar amounts of ethylene glycol and boric acid to form a borate ester chelate complex, adding said chelate complex in the presence of isopropyl alcohol to an ether amine of the formula,

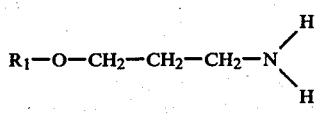

wherein $R_1$ is a straight or branched-chain alkyl radical and wherein the weight ratio of isopropyl alcohol to said ether amine is between 0.01:1 and 0.15:1, said method being reacted at a temperature of between 70° C. and 120° C., and at a gauge pressure of between 20 and 50 pounds per square inch, and adding ethylene oxide to said amine and said chelate complex.

* * * * *